United States Patent [19]

Donn

[11] Patent Number: 5,739,082
[45] Date of Patent: Apr. 14, 1998

[54] METHOD OF IMPROVING THE YIELD OF HERBICIDE-RESISTANT CROP PLANTS

[75] Inventor: Günter Donn, Hofheim, Germany

[73] Assignee: Hoechst Schering AgrEvo GmbH, Berlin, Germany

[21] Appl. No.: 583,076

[22] PCT Filed: Aug. 5, 1994

[86] PCT No.: PCT/EP94/02598

§ 371 Date: Apr. 25, 1996

§ 102(e) Date: Apr. 25, 1996

[87] PCT Pub. No.: WO95/05082

PCT Pub. Date: Feb. 23, 1995

Related U.S. Application Data

[63] Continuation-in-part of Ser. No. 279,706, Jul. 25, 1994, Pat. No. 5,633,434, which is a continuation of Ser. No. 123,699, Sep. 17, 1993, abandoned, which is a continuation of Ser. No. 910,329, filed as PCT/EP91/00130, Jan. 24, 1991, abandoned.

[30] Foreign Application Priority Data

Feb. 2, 1990 [DE] Germany ............ 40 03 045.8
Sep. 12, 1993 [DE] Germany ............ 43 27 056.5

[51] Int. Cl.$^6$ ........................... A01N 57/20
[52] U.S. Cl. ............................... 504/206
[58] Field of Search ............................ 504/206

[56] References Cited

U.S. PATENT DOCUMENTS

| | | | |
|---|---|---|---|
| 4,168,963 | 9/1979 | Rupp et al. | 71/86 |
| 4,400,196 | 8/1983 | Albrecht et al. | 71/86 |
| 4,764,620 | 8/1988 | Logusch | 548/113 |
| 5,145,777 | 9/1992 | Goodman et al. | 435/172.3 |
| 5,273,894 | 12/1993 | Strauch et al. | 435/129 |
| 5,276,268 | 1/1994 | Strauch et al. | 800/205 |
| 5,369,082 | 11/1994 | Frisch et al. | 504/127 |
| 5,489,520 | 2/1996 | Adams et al. | 435/172.3 |
| 5,502,271 | 3/1996 | Donn | 800/200 |
| 5,550,318 | 8/1996 | Adams et al. | 800/205 |
| 5,633,434 | 5/1997 | Schneider et al. | 800/205 |

FOREIGN PATENT DOCUMENTS

| | | |
|---|---|---|
| 242246 | 10/1987 | European Pat. Off. |
| 0242236 | 12/1987 | European Pat. Off. |
| 0275957 | 7/1988 | European Pat. Off. |
| 0290986 | 11/1988 | European Pat. Off. |
| 0481407 | 4/1992 | European Pat. Off. |
| 3200486 | 7/1983 | Germany |
| WO 87/05327 | 9/1987 | WIPO |
| WO 95/05082 | 2/1995 | WIPO |

OTHER PUBLICATIONS

English Language Abstract No. DE 3200-486-A., 1982.
English Language Abstract No. EP 481407-A., 1990.
Potrykus, "Gene Transfer to Cereals: An Assessment", Bio/Technology 8:535-542 (1990).
Tumer et al., "Expression of Alfalfa Mosaic Virus Coat Protein Gene Confers Cross-Protection in Transgenic Tobacco and Tomato Plants", EMBO Journal, 6:1181-1188, (1987).
De Block, "Engineering Herbicide Resistance in Plants by Expression of a Detoxifying Enzyme", EMBO Journal, 6:2513-2518 (1987).
Loesch-Fries et al., "Expression of Alfalfa Virus RNA 4 in Transgenic Plants Confers Virus Resistance", EMBO Journal, 6:1845-1851 (1987).
Finnegan et al., Transgene Inactivation: Plants Fight Back?, Bio-Technology, 12:883-888 (1994).
Weising et al., "Foreign Genes in Plants: Transfer, Structure, Expression, and Applications," Annu. Rev. Genet. 1988, 22:421-77.
Thompson et al., "Characterization of the herbicide-resistance gene bar from Streptomyces hygroscopicus", The EMBO Journal 6(9): 2519-23 (1987).
Wendler et al., J. Plant Phys. 139:666-671 (1992).
Holt, Annu. Rev. Plant Physiol. Plant Mol. Biol., 1993, 44:203-29.
Kocher, 1989 BCPC Mono. No. 42 Amino Acid Biosynthesis Inhibitors, 173-182.
Nejidot et al., Physiologia Plantanum 80:662-668 (1990).
Wilson, T.M.A., PNAS USA, 90:3134-41 (1993).

Primary Examiner—S. Mark Clardy
Attorney, Agent, or Firm—Frommer Lawrence & Haug LLP

[57] ABSTRACT

Method of improving the yield of crop plants which are resistant to glutamine synthetase inhibitors, in which plants are treated with glutamine synthetase inhibitors at low application rates, and to the use of glutamine synthetase inhibitors for improving the yield of transgenic crop plants.

8 Claims, No Drawings

METHOD OF IMPROVING THE YIELD OF HERBICIDE-RESISTANT CROP PLANTS

CROSS REFERENCE TO RELATED APPLICATIONS

This application is based upon and claims priority from PCT application PCT/EP94/02598, filed Aug. 5, 1994, designating the U.S., and German application P 43 27 056.5, filed Aug. 12, 1993. This application is also a continuation-in-part of application Ser. No. 08/279,706, filed Jul. 25, 1994, now U.S. Pat. No. 5,633,434, which is a continuation of application Ser. No. 08/123,699, filed Sep. 17, 1993, abandoned, which is a continuation of application Ser. No. 07/910,329, filed Aug. 20, 1992, now abandoned, claiming priority from PCT/EP91/00130, filed Jan. 24, 1991 and designating the U.S., and from German application P 40 03 045.8, filed Feb. 2, 1990.

BACKGROUND OF THE INVENTION

The compound glufosinate (glufosinate-ammonium, ammonium DL-homoalanin-4-yl(methyl)phosphinate, Schwerdtle et al, Z. Pflanzenkr. Pflanzenschutz., 1981, Special Edition IX, page 431) acts as a glutamine synthetase (GS) inhibitor since it is a structural analog of glutamic acid. GS plays a central role in the metabolism of all plants. It is responsible for the detoxification of $NH_3$ is, and, as a consequence, all terrestrial plants are damaged severely or destroyed after application of glufosinate since the assimilation of ammonia is inhibited.

Plants which are resistant to the herbicidal activity of GS inhibitors were successfully produced by transferring and expressing a glufosinate acetyltransferase gene isolated from from strains of Streptomycetes which produce bialaphos (phosphinothricin-alanyl-alanine) (EP-B1-0 242 236 and EP-B1-0 257 542). Stands of such transgenic, herbicide-tolerant crop plants can be kept weed-free in an efficient manner by post-emergence treatment with glucosinate.

SUMMARY OF THE INVENTION

Unexpectedly, field trials with such transgenic plants showed that the glufosinate-treated plants give a measurably higher yield than untreated plant stands. This higher yield is not a result of the excellent weed control by glufosinate and its complete compatibility with the stands of transgenic crop plants, but a positive effect of the herbicide treatment on growth and yield.

The invention therefore relates to a method of improving the yield of crop plants which are resistant to glutamine synthetase inhibitors, which comprises treating the plants with glutamine synthetase inhibitors at application rates which are not harmful to the plants.

In particular, the invention relates to a method in which glutamine synthetase inhibitors are employed for a yield-improving treatment of plants which are protected against the herbicidal activity of the glutamine synthetase inhibitors by expression of an N-acetyltransferase gene.

The invention furthermore relates to the use of a glutamine synthetase inhibitor for improving the yield of crop plants which are resistant to this inhibitor. In particular, it relates to the use of glutamine synthetase inhibitors for improving the yield of transgenic crop plants.

DETAILED DESCRIPTION OF THE INVENTION

The glutamine synthetase inhibitor used is preferably the compound glufosinate or bialaphos (Tachibana et al, Abstr. 5th Int. Congr. Pestic. Chem., IVa, Abstract 19; Mase, Jpn. Pestic. Inf., 1984, No. 45, p. 27). In this context, the term glufosinate embraces the racemate (DL-homoalanin-4-yl (methyl)phosphinic acid as well as the biologically active L isomer and the corresponding salts. The herbicide can be employed in the commercially available formulations. A further example of a GS inhibitor is the compound phosalacin (Omura et al., J. of Antibiotics, Vol. 37, 8, pages 939–940, 1984).

The yield-improving effect of the treatment with glufosinate is particularly pronounced when the herbicidal treatment is carried out in the 2 to 8-, preferably the 3 to 6-leaf stage of the crop plants before flowering or, in the case of perennial plants, at any desired point in time.

In the method according to the invention, the plants are treated at least once with the herbicide at application rates as they are also employed for weed control, for example 150 g–1000 g of glufosinate/ha.

However, the application rate required may vary as a function of the plants, their height and the climatic conditions.

It is particularly advantageous to carry out the process using application rates of 350–700 g of glufosinate/ha. Within this range of application rates, the effect achieved is proportional to the application rate of glufosinate, but not based on differences in the level of weed control. It is possible to achieve a weed control effect which is similar to the effect which can be achieved at higher application rates even when the application rate of PTC is low.

It is particularly advantageous to treat the plants repeatedly with low dosages in the lower range of the application concentrations, the treatment interval being a few days, i.e. between 2 and 30 days, preferably between 5 and 20, particularly preferably between 8 and 15 days. It is particularly advantageous to treat the plants with low dosages, the treatment interval being from 9 to 11 days.

The method according to the invention can generally be used for the treatment of plants which are resistant to GS inhibitors. Resistant plants can also be obtained by conventional breeding methods. If the resistance level of plant obtained by conventional selection is similar to that of the transgenic plants, the plants obtained by conventional selection can also be treated by the method according to the invention. However, the method is particularly suitable for the treatment of glufosinate-resistant plants which have been obtained by transferring a gene for resistance to the herbicide. EP-B1-0 242 236 and EP-B1-0 257 542 describe methods for producing such plants.

In this context, the term plants embraces crop plants from the group of the angiosperms and the gymnosperms. The method according to the invention allows individual plants, but also crops of plants, to be treated.

Particularly interesting among the gymnosperms is the class of the conifers.

Particularly interesting among the angiosperms are the plants from the families of the Solanaceae, Cruciferae, Compositae, Liliaceae, Vitaceae, Chenopodiaceae, Rutaceae, Bromeliaceae, Rubiaceae, Theaceae, Musaceae or Gramineae and the order of the Leguminosae. Representatives of the families Solanaceae, Cruciferae and Gramineae are preferably treated.

The method is of particular interest for the treatment of crop plants in which high yields are important, such as, for example, maize, soybeans, spring and winter oil seed rape, sugar beet, lucerne, sunflower, cotton, potatoes, wheat, barley and rice. However, it can also be used advantageously in tomatoes and other vegetables, such as cucumber, and fruits, such as melon, strawberries, raspberries, and kiwi fruit.

The use of the method in herbicide-resistant woody species is also particularly important, for example in plantations and nurseries.

Application of GS inhibitors, such as, for example, PTC and its analogs and derivatives, to young specimens of woody species can accelerate the juvenile development. In this context, mention must be made, in particular, of walnut trees, oil palms, fruit trees, poplars and other cultivated plants which are woody species.

The method according to the invention is therefore important both in agriculture and horticulture since application of the herbicidal glutamine synthetase inhibitor allows a clearly measurable increase in yield to be achieved without an additional application of fertilizer and plant growth regulators. The term increase in yield means in this context that the plant yield up to 50% more. Herbicides having different mechanisms of action either do not show such an effect or, frequently, have an adverse effect on yield.

The growth-enhancing activity of the glufosinate treatment can be measured in field trials and pot trials, by comparing yields of stands of plants which are treated with conventional herbicides or which were kept free from weeds by non-chemical methods.

The examples which follow are intended to illustrate the invention without thereby imposing any restriction.

EXAMPLE 1

Transgenic glufosinate-tolerant maize or soybean plants were planted in plots (10 m$^2$) and, in the 3–5 leaf stage, treated with various amounts of glufosinate. The weed control level was scored 42 days after the application. When the crops were ripe, the plots were harvested, and the seed yield was determined by weighing the kernels obtained.

When the maize plants were examined, Laddock® (a mixture of atrazine and bentazone) was employed as comparison product. Two products were employed for the treatment of the soya bean plants. Comparison product 1 contained a mixture of 134 g of fenoxaprop-P-ethyl/ha and 425 g of fomesafen/ha; comparison product 2 contained 2240 g of metolachlor/ha and 840 g of Storm® (a mixture of bentazone and acifluorfen)/ha. The comparison products are known from "The Pesticide Manual", 9th Edition, Brit. Crop Prot. Council, 1991.

The treatment described in Table 2, in which two low glufosinate dosage rates were used, was carried out at a 10 day interval.

TABLE 1

| | Application rates of Comparison glufosinate (g of active substance/ha) | | | Comparison product |
|---|---|---|---|---|
| | 150 | 450 | 650 | |
| Weed control level in % | 92 | 97 | 98 | 78 |
| Yield in % of the plot with the comparison product | 118 | 121 | 125 | 100 |

TABLE 2

Grain yield of glufosinate-tolerant soybean plants after application of glufosinate

| | Application rates of glufosinate: g of active substance/ha | | | | | | | | Comparison product | |
|---|---|---|---|---|---|---|---|---|---|---|
| | 350 | 450 | 550 | 650 | 150 + 150 | 250 + 250 | 350 + 350 | 450 + 450 | 1 | 2 |
| Weed control level in % | 85 | 93 | 95 | 94 | 96 | 96 | 98 | 99 | 98 | 90 |
| Yield in % (based on plot with comparison product 1) | 88 | 108 | 120 | 132 | 104 | 132 | 148 | 152 | 100 | 92 |

I claim:

1. A method of improving the growth of crop plants which are transformed so as to be resistant to glutamine synthetase inhibitors, which comprises treating the plants with a growth stimulating amount of a glutamine synthetase inhibitor.

2. A method as claimed in claim 1, wherein glufosinate or salts thereof are employed in treating the plants and the plants are resistant to glutamine synthetase inhibitors by expression of n-acetyltransferase.

3. A method as claimed in claim 1, wherein the treating is performed at least once at an application rate of the glutamine synthetase inhibitor as is also employed for weed control.

4. A method as claimed in claim 1, wherein the crop plants are treated at least once with 150–1000 g of glufosinate/ha.

5. The method as claimed in claim 1, wherein the crop plants are treated at least once with 350–700 g of glufosinate/ha.

6. The method as claimed in claim 1, further comprising the steps of:
   transforming plant cells so that the cells contain an isolated DNA molecule consisting of a nucleotide sequence coding for n-acetyltransferase;
   selecting transformed cells; and
   regenerating the plants from the cells,
before treating the regenerated plants with a phosphinothricin herbicide.

7. The method as claimed in claim 6, wherein the coding for the n-acetyltransferase is from Streptomyces.

8. The method as claimed in claim 6, wherein the phosphinothricin herbicide is glufosinate or a salt thereof.

* * * * *

(12) EX PARTE REEXAMINATION CERTIFICATE (8990th)
United States Patent
Donn

(10) Number: US 5,739,082 C1
(45) Certificate Issued: May 1, 2012

(54) METHOD OF IMPROVING THE YIELD OF HERBICIDE-RESISTANT CROP PLANTS

(75) Inventor: Günter Donn, Hofheim (DE)

(73) Assignee: Bayer Cropscience AG, Monheim (DE)

Reexamination Request:
No. 90/011,930, Oct. 28, 2011

Reexamination Certificate for:
Patent No.: 5,739,082
Issued: Apr. 14, 1998
Appl. No.: 08/583,076
Filed: Apr. 25, 1996

(22) PCT Filed: Aug. 5, 1994

(86) PCT No.: PCT/EP94/02598

§ 371 (c)(1),
(2), (4) Date: Apr. 25, 1996

(87) PCT Pub. No.: WO95/05082

PCT Pub. Date: Feb. 23, 1995

Related U.S. Application Data

(63) Continuation-in-part of application No. 08/279,706, filed on Jul. 25, 1994, now Pat. No. 5,633,434, which is a continuation of application No. 08/123,699, filed on Sep. 17, 1993, now abandoned, which is a continuation of application No. 07/910,329, filed on Aug. 20, 1992, now abandoned.

(30) Foreign Application Priority Data

Feb. 2, 1990 (DE) .......................................... 40 03 045
Sep. 12, 1993 (DE) .......................................... 43 27 056

(51) Int. Cl.
*C07K 14/005* (2006.01)
*C07K 14/08* (2006.01)
*A01N 57/20* (2006.01)
*A01N 57/00* (2006.01)
*C12N 9/10* (2006.01)
*C12N 15/82* (2006.01)

(52) U.S. Cl. ...................................................... 504/206
(58) Field of Classification Search ........................ None
See application file for complete search history.

(56) References Cited

To view the complete listing of prior art documents cited during the proceeding for Reexamination Control Number 90/011,930, please refer to the USPTO's public Patent Application Information Retrieval (PAIR) system under the Display References tab.

*Primary Examiner* — Bruce Campell

(57) ABSTRACT

Method of improving the yield of crop plants which are resistant to glutamine synthetase inhibitors, in which plants are treated with glutamine synthetase inhibitors at low application rates, and to the use of glutamine synthetase inhibitors for improving the yield of transgenic crop plants.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *

US005739082C2

(12) EX PARTE REEXAMINATION CERTIFICATE (10328th)
United States Patent
Donn

(10) Number: US 5,739,082 C2
(45) Certificate Issued: Oct. 14, 2014

(54) METHOD OF IMPROVING THE YIELD OF HERBICIDE-RESISTANT CROP PLANTS

(75) Inventor: Günter Donn, Hofheim (DE)

(73) Assignee: Bayer Cropscience AG, Monheim (DE)

Reexamination Request:
No. 90/012,978, Oct. 1, 2013

Reexamination Certificate for:
Patent No.: 5,739,082
Issued: Apr. 14, 1998
Appl. No.: 08/583,076
Filed: Mar. 12, 1996

Reexamination Certificate C1 5,739,082 issued May 1, 2012

(21) Appl. No.: 90/012,978

(22) PCT Filed: Aug. 5, 1994

(86) PCT No.: PCT/EP94/02598
§ 371 (c)(1),
(2), (4) Date: Apr. 25, 1996

(87) PCT Pub. No.: WO95/05082
PCT Pub. Date: Feb. 23, 1995

Related U.S. Application Data

(63) Continuation-in-part of application No. 08/279,706, filed on Jul. 25, 1994, now Pat. No. 5,633,434, which is a continuation of application No. 08/123,699, filed on Sep. 17, 1993.

(30) Foreign Application Priority Data

Feb. 2, 1990 (DE) .................................... 40 03 045
Sep. 12, 1993 (DE) .................................... 43 27 056

(51) Int. Cl.
| | | |
|---|---|---|
| *C07K 14/005* | (2006.01) | |
| *A01N 57/20* | (2006.01) | |
| *C07K 14/08* | (2006.01) | |
| *C12N 9/10* | (2006.01) | |
| *C12N 15/82* | (2006.01) | |
| *A01N 57/00* | (2006.01) | |

(52) U.S. Cl.
USPC ......................................................... 504/206

(58) Field of Classification Search
None
See application file for complete search history.

(56) References Cited

To view the complete listing of prior art documents cited during the proceeding for Reexamination Control Number 90/012,978, please refer to the USPTO's public Patent Application Information Retrieval (PAIR) system under the Display References tab.

*Primary Examiner* — Bruce Campell

(57) ABSTRACT

Method of improving the yield of crop plants which are resistant to glutamine synthetase inhibitors, in which plants are treated with glutamine synthetase inhibitors at low application rates, and to the use of glutamine synthetase inhibitors for improving the yield of transgenic crop plants.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 3 is cancelled.

Claims 1, 2, 4 and 5 are determined to be patentable as amended.

Claims 6-8, dependent on an amended claim, are determined to be patentable.

New claims 9-19 are added and determined to be patentable.

1. A method of improving the growth of crop plants which are transformed so as to be resistant to glutamine synthetase inhibitors, which comprises treating the plants with a growth stimulating amount of a glutamine synthetase inhibitor, *wherein the glutamine synthase inhibitor is glufosinate or a salt thereof and wherein crop plants are treated at least once with the glufosinate at a concentration of at least 450 g/ha*.

2. [A] *The* method as claimed in claim 1, wherein glufosinate or salts thereof are employed in treating the plants and the plants are resistant to glutamine synthetase inhibitors by expression of n-acetyltransferase.

4. [A] *The* method as claimed in claim 1, wherein the crop plants are treated at least once with [150-1000] *450-1000* g of glufosinate/ha.

5. The method as claimed in claim 1, wherein the crop plants are treated at least once with [350-700] *450-650* g of glufosinate/ha.

9. *The method as claimed in claim 1, wherein the crop plant is soybean.*

10. *The method as claimed in claim 1, wherein the crop plant is cotton.*

11. *The method as claimed in claim 1, wherein the crop plant is maize.*

12. *A method of improving the growth of crop plants which are transformed so as to be resistant to glutamine synthetase inhibitors, which comprises treating the plants with a growth stimulating amount of a glutamine synthetase inhibitor, wherein the glutamine synthetase inhibitor is glufosinate or salts thereof and wherein the crop plants are treated at least twice at a concentration of at least 150 g of glufosinate/ha.*

13. *The method as claimed in claim 12, wherein glufosinate or salts thereof are employed in treating the plants and the plants are resistant to glutamine synthetase inhibitors by expression of n-acetyltransferase.*

14. *The method as claimed in claim 12, wherein the crop plants are treated at least twice with 150-450 g of glufosinate/ha.*

15. *The method as claimed in claim 12, further comprising the steps of:*
   *transforming plant cells so that the cells contain an isolated DNA molecule consisting of a nucleotide sequence coding for n-acetyltransferase;*
   *selecting transformed cells; and*
   *regenerating the plants from the cells, before treating the regenerated plants with a phosphinothricin herbicide.*

16. *The method as claimed in claim 15, wherein the coding for the n-acetyltransferase is from Streptomyces.*

17. *The method as claimed in claim 12, wherein the crop plant is soybean.*

18. *The method as claimed in claim 12, wherein the crop plant is cotton.*

19. *The method as claimed in claim 12, wherein the crop plant is maize.*

* * * * *